United States Patent
Kubota et al.

(10) Patent No.: US 11,142,464 B2
(45) Date of Patent: Oct. 12, 2021

(54) BETA ZEOLITE, METHOD FOR PRODUCING SAME, AND CATALYST

(71) Applicants: Mitsui Mining & Smelting Co., Ltd., Tokyo (JP); NATIONAL UNIVERSITY CORPORATION YOKOHAMA NATIONAL UNIVERSITY, Yokohama (JP)

(72) Inventors: Yoshihiro Kubota, Kanagawa (JP); Satoshi Inagaki, Kanagawa (JP); Yuya Ikehara, Kanagawa (JP); Mei Takeyama, Kanagawa (JP); Yasuo Yamazaki, Tokyo (JP)

(73) Assignees: Mitsui Mining & Smelting Co., Ltd., Tokyo (JP); NATIONAL UNIVERSITY CORPORATION YOKOHAMA NATIONAL UNIVERSITY, Kanagawa (JP)

( * ) Notice: Subject to any disclaimer, the term of this patent is extended or adjusted under 35 U.S.C. 154(b) by 0 days.

(21) Appl. No.: 16/758,200

(22) PCT Filed: Oct. 25, 2018

(86) PCT No.: PCT/JP2018/039778
§ 371 (c)(1),
(2) Date: Apr. 22, 2020

(87) PCT Pub. No.: WO2019/082995
PCT Pub. Date: May 2, 2019

(65) Prior Publication Data
US 2020/0339431 A1   Oct. 29, 2020

(30) Foreign Application Priority Data
Oct. 25, 2017   (JP) .............................. JP2017-206339

(51) Int. Cl.
| | | |
|---|---|---|
| *B01J 29/70* | (2006.01) | |
| *C01B 39/46* | (2006.01) | |
| *B01J 37/30* | (2006.01) | |
| *C07C 37/60* | (2006.01) | |
| *C07C 39/08* | (2006.01) | |

(52) U.S. Cl.
CPC ........... *C01B 39/46* (2013.01); *B01J 29/7057* (2013.01); *B01J 37/30* (2013.01); *C07C 37/60* (2013.01); *B01J 2229/10* (2013.01); *B01J 2229/16* (2013.01); *B01J 2229/18* (2013.01); *B01J 2229/183* (2013.01); *B01J 2229/20* (2013.01); *B01J 2229/37* (2013.01); *C07C 39/08* (2013.01); *Y02P 20/52* (2015.11)

(58) Field of Classification Search
CPC .... B01J 29/7057; B01J 29/89; B01J 2229/10; B01J 2229/16; B01J 2229/18; B01J 2229/183; B01J 2229/37; C01B 39/08; C01B 39/46; C01B 39/026; Y02P 20/52; C07C 37/60; C07C 39/08; C07B 61/00; C07D 303/04; C07D 301/12
USPC .............. 502/60, 85, 86; 423/700, 713, 714; 568/376, 798, 800
See application file for complete search history.

(56) References Cited

U.S. PATENT DOCUMENTS

| | | |
|---|---|---|
| 3,308,069 A | 3/1967 | Wadlinger et al. |
| 5,374,747 A | 12/1994 | Saxton et al. |
| 5,412,122 A | 5/1995 | Saxton et al. |
| 5,453,511 A | 9/1995 | Saxton |
| 2010/0322847 A1 | 12/2010 | Xiao et al. |
| 2012/0190534 A1 | 7/2012 | Itabashi et al. |
| 2013/0156690 A1 | 6/2013 | Itabashi et al. |
| 2014/0322126 A1 | 10/2014 | Kubota et al. |

FOREIGN PATENT DOCUMENTS

| | | |
|---|---|---|
| JP | H07-242649 A | 9/1995 |
| JP | 2012-530035 A | 11/2012 |
| WO | 2011/013560 A1 | 2/2011 |
| WO | 2012/002367 A1 | 1/2012 |
| WO | 2013/077404 A1 | 5/2013 |

OTHER PUBLICATIONS

International Search Report (ISR) dated Dec. 11, 2018 filed in PCT/JP2018/039778.
Yilmaz et al., "A new catalyst platform: zeolite Beta from template-free synthesis", Catalysis Science & Technology, 2013, vol. 3, No. 10, pp. 2580-2586; Cited in EESR.
Extended European Search Report (EESR) dated Oct. 23, 2020 issued in the corresponding European Patent Application No. 18871561.9.
Indian Office Action (INOA) dated Oct. 31, 2020 issued in the corresponding Indian Patent Application No. 202047021238.

*Primary Examiner* — Elizabeth D Wood
(74) *Attorney, Agent, or Firm* — Rankin, Hill & Clark LLP (57) ABSTRACT

Provided is a beta zeolite also having exceptional catalytic activity as a catalyst other than an olefin epoxidation catalyst. This beta zeolite is synthesized without using an organic structure-directing agent and has titanium in the structural skeleton thereof, the Ti content being 0.10 mmol/g or higher. This beta zeolite preferably has an Si/Ti molar ratio of 20-200. Also, the Si/Al molar ratio is preferably 100 or higher.

9 Claims, 8 Drawing Sheets

FIG. 4
EXAMPLE 1

BETA ZEOLITE, METHOD FOR PRODUCING SAME, AND CATALYST

CROSS-REFERENCE TO RELATED APPLICATIONS

This application is a National Phase Application of International Application No. PCT/JP2018/039778, filed Oct. 25, 2018, which claims the priority of Japan Patent Application No. 2017-206339, filed Oct. 25, 2017. The present application claims priority from both applications and each of these applications is herein incorporated in their entirety by reference.

TECHNICAL FIELD

The present invention relates to a Ti-containing beta zeolite and a catalyst including the same. The present invention also relates to a method for producing the beta zeolite.

BACKGROUND ART

Beta zeolites, which are useful as solid acid catalysts and adsorbents, are currently used in large quantities worldwide as catalysts in the petrochemical industry and as hydrocarbon traps for purifying exhaust gas from internal combustion engines. Various methods are proposed for the synthesis of beta zeolites. A common method uses a tetraethylammonium ion-containing compound as a structure-directing agent (hereinafter abbreviated as "organic SDA"). Such a method is described, for example, in Patent Document 1 listed below. However, the tetraethylammonium ion-containing compound is not only expensive but also not recoverable or reusable because, after the crystallization of beta zeolite is completed, most of its excess is decomposed and the fraction of it incorporated in the crystals cannot be removed by any method other than decomposition. Therefore, the beta zeolite produced by this method is expensive. Further, the tetraethylammonium ions are incorporated into the crystals and thus need to be removed by firing in order for the beta zeolite to be used as an adsorbent or a catalyst. Exhaust gas produced in this process can cause environmental pollution, and many chemicals will be needed for making the synthesis mother liquor unharmful. As described above, the method for synthesizing beta zeolite using tetraethylammonium ions is not only expensive but also has a large impact on the environment, and therefore, there has been a demand for providing a production method without using any organic SDA.

Under these circumstances, Patent Document 2 recently proposed a method for synthesizing a beta zeolite without using any organic SDA. This document discloses a method for synthesizing a beta zeolite without using any organic SDA, including: mixing a silica source, an alumina source, an alkali source, and water to form a reactant mixture with a specific composition; adding 0.1 to 20% by mass of organic compound-free beta zeolite seed crystals having a $SiO_2/Al_2O_3$ ratio of 8 to 30 and a mean particle size of 150 nm or more to the reactant mixture based on the mass of the silica component in the reactant mixture; and heating the reactant mixture with the added seed crystals in a closed system at 100 to 200° C.

On the other hand, a beta zeolite produced using an organic SDA and containing titanium in its structural skeleton is conventionally considered to have high catalytic activity, and proposed to be used, for example, as an olefin epoxidation catalyst (see Patent Document 3).

Patent Document 1: U.S. Pat. No. 3,308,069
Patent Document 2: Pamphlet of PCT International Publication No. WO2011/013560
Patent Document 3: Japanese Unexamined Patent Application, Publication No. H07-242649

DISCLOSURE OF THE INVENTION

Problems to be Solved by the Invention

However, such a beta zeolite has been required to have a catalytic function other than that for epoxidation of olefins.

It is an object of the present invention to provide a zeolite that can be free from various disadvantages of the above conventional techniques and to provide a method for producing such a zeolite.

Means for Solving the Problems

The present invention provides a beta zeolite including a titanium-containing structural skeleton and having a Ti content of 0.10 mmol/g or more, the beta zeolite being synthesized without using any organic structure-directing agent.

The present invention also provides a catalyst for oxidation of phenols, including the beta zeolite, and a catalyst for epoxidation of olefins, including the beta zeolite.

Further, the present invention provides a method for producing the beta zeolite, including: performing ion exchange on a raw material beta zeolite synthesized without using any organic structure-directing agent to form an ammonium-type beta zeolite; then exposing the ammonium-type beta zeolite to water vapor; performing an acid treatment on the beta zeolite after the exposure; and then introducing Ti into the beta zeolite after the acid treatment.

Effects of the Invention

According to the present invention, there is provided a beta zeolite having high catalytic activity for other purposes in addition to epoxidation of olefins. The method of the present invention for producing the beta zeolite makes it possible to produce the beta zeolite of the present invention by an industrially advantageous method.

BRIEF DESCRIPTION OF THE DRAWINGS

FIG. 5 is a graph showing nitrogen adsorption-desorption isotherms of Ti-containing beta zeolites of Example 1 and so on;

FIG. 6 is a graph showing water vapor adsorption-desorption isotherms of Ti-containing beta zeolites of Example 1 and so on;

PREFERRED MODE FOR CARRYING OUT THE INVENTION

The Ti-containing beta zeolite of the present invention contains Ti in its structural skeleton and has high levels of different catalytic activities. The presence of Ti in the skeletal structure of the beta zeolite can be checked by measuring the UV spectrum of the zeolite and observing a peak at 205 nm to 230 nm in the spectrum. Hereinafter, the Ti-containing beta zeolite of the present invention is also referred to as "the Ti-containing beta zeolite".

The Ti-containing beta zeolite of the present invention has a Ti content of 0.10 mmol/g or more. Thanks to the presence of Ti in the structural skeleton and such a high Ti content, the Ti-containing beta zeolite of the present invention is more useful as a catalyst for oxidation of hydrocarbons in the petrochemical industry. That is, the presence of more Ti atoms in the skeleton can enhance the catalytic activity of the zeolite as a whole. From this point of view, the Ti-containing beta zeolite preferably has a Ti content of 0.15 mmol/g or more, in particular preferably 0.20 mmol/g or more. The content of Ti in the beta zeolite preferably has an upper limit as high as possible. For example, the Ti content preferably has a high upper limit of about 0.50 mmol/g or a low upper limit of about 0.30 mmol/g. In this case, the production cost for further increasing the Ti content can be saved while sufficiently high performance can be achieved even if the Ti content is not higher than that. The beta zeolite having a Ti content of 0.10 mmol/g or more can be produced by a preferred method described later.

The Ti-containing beta zeolite of the present invention further preferably has a Si/Al molar ratio of 100 or more. With such a high Si/Al molar ratio, the Ti-containing beta zeolite of the present invention can be highly useful as a catalyst for oxidation of hydrocarbons in the petrochemical industry. In this regard, it is well known that aluminum serves as an inhibitor of the function of beta zeolites to catalyze the oxidation of phenols, in particular, phenol. Therefore, in order to use the beta zeolite as a catalyst for oxidation of phenols, in particular, phenol, the aluminum content of the beta zeolite should be reduced as much as possible if the beta zeolite is a common aluminosilicate. From this point of view, the Ti-containing beta zeolite preferably has a Si/Al molar ratio of 300 or more, in particular preferably 500 or more. The Si/Al molar ratio is preferably as high as possible and has no specific upper limit. The Si/Al molar ratio may be measured by the method described later. When the Si/Al molar ratio is to be accurately measured by the method described later, the detection limit is approximately 1,000. The beta zeolite having a Si/Al molar ratio equal to or more than the lower limit mentioned above can be produced by a preferred method described later.

The Ti-containing beta zeolite of the present invention is synthesized without using any organic structure-directing agent. The inventors believe that the Ti-containing beta zeolite of the present invention has high catalytic activity because of less defects. The term "synthesized without using any organic structure-directing agent" specifically means that no organic structure-directing agent is contained in the raw materials for its synthesis. Therefore, for example, even when a raw material includes a seed crystal produced using an organic structure-directing agent, the organic structure-directing agent can be removed by firing the seed crystal before use, and other raw materials can be free of any organic structure-directing agent. The term "synthesized without using any organic structure-directing agent" is intended to include such a case. The present inventors have found that Ti-containing beta zeolites synthesized without using any organic structure-directing agent are superior to Ti-containing beta zeolites synthesized using an organic structure-directing agent in terms of catalytic activity, in particular, catalytic activity for phenols. While the description shows preferred structures and properties of the Ti-containing beta zeolite of the present invention as much as possible, there are circumstances where it takes unduly high cost and long period of time and thus is impossible to determine further structures and properties of the Ti-containing beta zeolite. In light of the nature of patent application, such as the need for prompt filing, the description discloses preferred features of the Ti-containing beta zeolite of the present invention as shown above, as well as shows that the present invention is directed to a Ti-containing beta zeolite synthesized without using any organic structure-directing agent as mentioned above.

The Ti-containing beta zeolite of the present invention preferably has a substantially octahedral structure or a truncated octahedral structure when observed with a scanning electron microscope. Commonly, beta zeolites obtained using a structure-directing agent do not have such a substantially octahedral structure or truncated octahedral structure. The observation is preferably performed, for example, with a magnification of 5,000 to 100,000.

The Ti-containing beta zeolite of the present invention preferably has a Si/Ti molar ratio of 20 or more in order to prevent deposition of Ti outside the skeleton. Further, the Si/Ti molar ratio is preferably 200 or less in order to make the effect of Ti sufficient. For these reasons, the Si/Ti molar ratio is more preferably 30 or more and 150 or less, in particular preferably 50 or more and 80 or less. The beta zeolite with a Si/Ti molar ratio in the above ranges can be produced by a preferred method described later.

The Si/Al molar ratio, the Si/Ti molar ratio, and the Ti content can be measured by an ICP-AES method, for example, according to the method described below in the EXAMPLES section.

Figure 5:
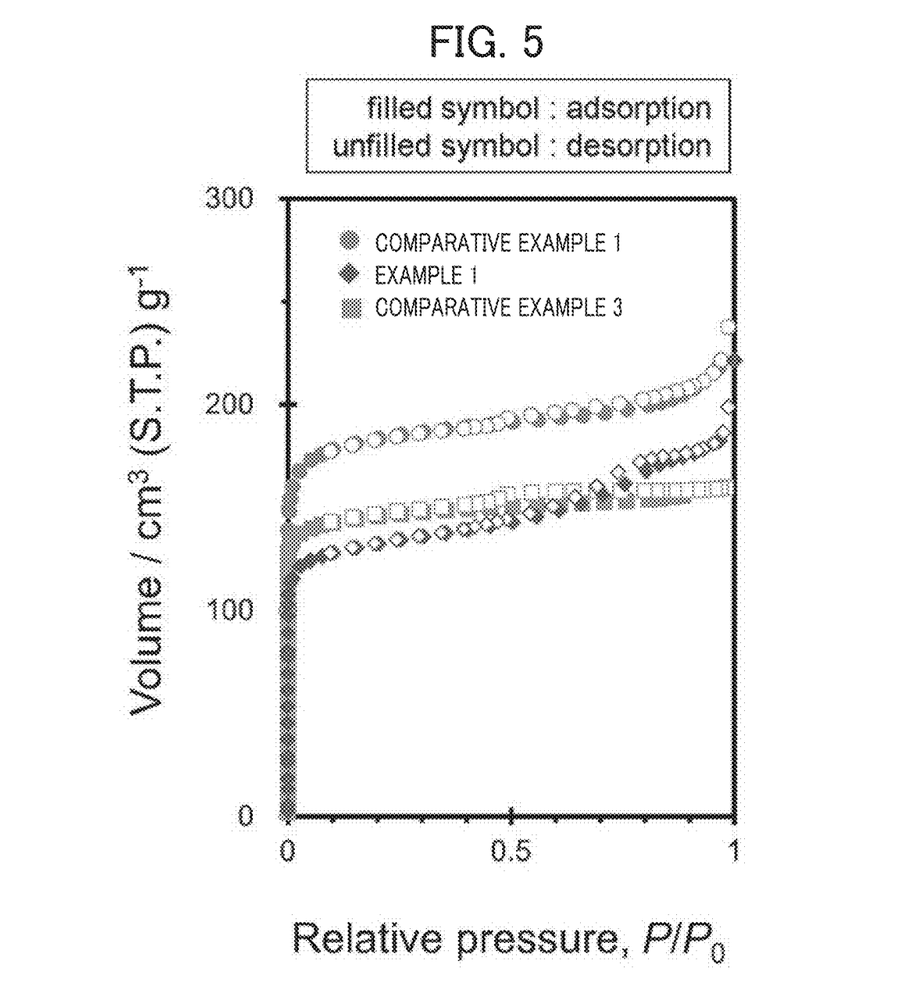

The beta zeolite preferably has a nitrogen adsorption isotherm at −196° C. that shows a nitrogen absorption of 100 to 195 cm$^3$ (STP)/g at a relative pressure P/P$_0$ of 0.4 and shows a nitrogen absorption of 150 to 220 cm$^3$ (STP)/g at a relative pressure P/P$_0$ of 0.9, in which P and P$_0$ are respectively the equilibrium pressure and the saturated vapor pressure at a temperature of −196° C. More preferably, the beta zeolite has a nitrogen adsorption isotherm at −196° C. that shows a nitrogen absorption of 100 to 175 cm$^3$ (STP)/g at a relative pressure P/P$_0$ of 0.4 and shows a nitrogen absorption of 160 to 220 cm$^3$ (STP)/g at a relative pressure P/P$_0$ of 0.9, in which P and P$_0$ are respectively the equilibrium pressure and the saturated vapor pressure at a temperature of −196° C. As shown in FIG. 5 described later, conventional Ti-containing beta zeolites do not show such adsorption levels. Such an increase in adsorption between relative pressures P/P$_0$ of 0.4 and 0.9 observed in the nitrogen adsorption isotherm may be attributed to the presence of mesopores. The nitrogen adsorption isotherm of the beta zeolite may be measured using a BET surface area analyzer, specifically, according to the method described in the EXAMPLES section.

Figure 6:
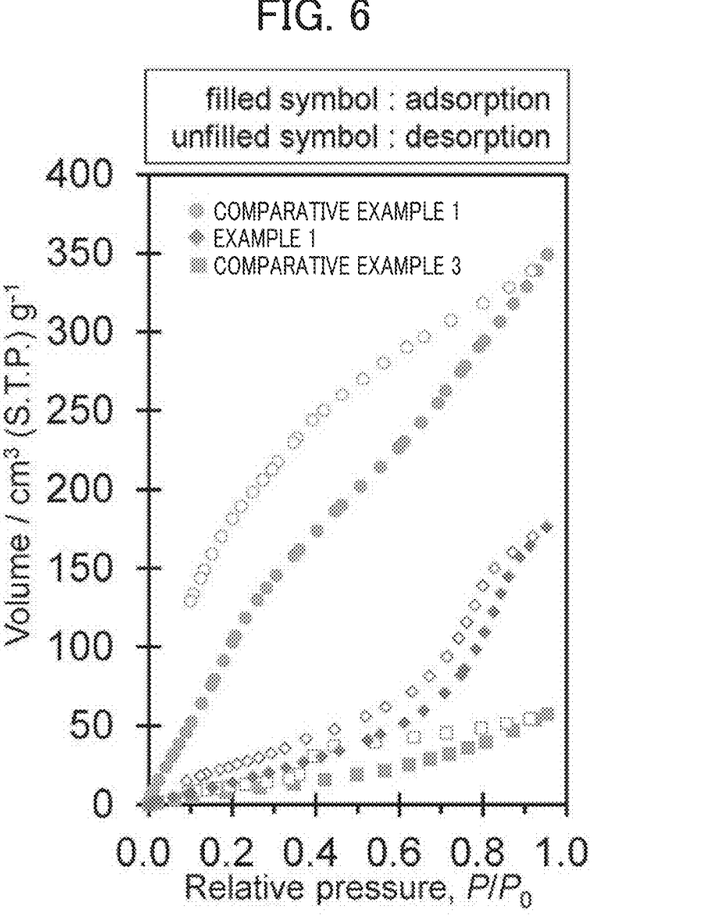

The beta zeolite preferably has a water vapor adsorption isotherm at 25° C. that shows a water absorption of 5 to 180 cm$^3$ (STP)/g at a relative pressure P/P$_0$ of 0.4 and shows a water absorption of 45 to 335 cm³ (STP)/g at a relative pressure P/P₀ of 0.9, in which P and P₀ are respectively the equilibrium pressure and the saturated vapor pressure at a temperature of 25° C. More preferably, the beta zeolite has a water vapor adsorption isotherm at 25° C. that shows a water absorption of 30 to 50 cm³ (STP)/g at a relative pressure P/P₀ of 0.4 and shows a water absorption of 135 to 190 cm³ (STP)/g at a relative pressure P/P₀ of 0.9, in which P and P₀ are respectively the equilibrium pressure and the saturated vapor pressure at a temperature of 25° C. As shown in FIG. 6 described later, conventional Ti-containing beta zeolites do not show such adsorption levels. Such an increase in adsorption between relative pressures P/P₀ of 0.4 and 0.9 observed in the water vapor adsorption isotherm may be attributed to capillary condensation occurring in mesopores. The water vapor adsorption isotherm of the beta zeolite is preferably classified as type III according to the IUPAC classification.

The nitrogen adsorption-desorption isotherm of the beta zeolite preferably has hysteresis. This suggests that the beta zeolite has mesopores. The nitrogen adsorption-desorption isotherm and the water vapor adsorption-desorption isotherm can be measured by the method shown below in the EXAMPLES section. The beta zeolite having the characteristics of the nitrogen adsorption-desorption isotherm and the water vapor adsorption-desorption isotherm described above can be produced by a preferred method described later.

The beta zeolite preferably has a $^{29}$Si DD MAS NMR spectrum with two or more peaks observed in the range of −114 ppm to −110 ppm when hexamethyltricyclosiloxane (−9.66 ppm) is used as a reference. The peaks in this range are derived from repeating structures composed of Si and oxygen atoms in the beta zeolite. The two or more peaks observed in this range suggest that the repeating structures composed of Si and oxygen atoms are highly uniform. Therefore, the two or more peaks observed in this range may contribute to the high catalytic activity of the Ti-containing beta zeolite of the present invention.

The beta zeolite also preferably has a $^{29}$Si DD MAS NMR spectrum with no peak observed in the range of −108 ppm to −100 ppm or a $^{29}$Si DD MAS NMR spectrum with a peak observed in the range of −108 ppm to −100 ppm with a height of 3.0% or less, in particular preferably 2.5% or less of the height of the main peak observed at −114 ppm to −110 ppm. The peak in the range of −108 ppm to −100 ppm is derived from silanol groups, which do not contribute to the structural skeleton formation. On the other hand, the introduction of titanium probably reduces the number of silanol groups or silicon atoms, which do not contribute to structural skeleton formation. The beta zeolite having a $^{29}$Si DD MAS NMR spectrum with the above characteristics can be produced by a preferred method described later.

As described above, the Ti-containing beta zeolite of the present invention may be characterized by both (i) being synthesized without using any organic structure-directing agent and (ii) having a Si/Al molar ratio of 100 or more. None of beta zeolites known so far have both characteristics. The present inventors have found that beta zeolites having both characteristics (i) and (ii) have high catalytic activity, in particular, high catalytic activity for oxidation of phenols, and as a result, have completed the present invention.

The Ti-containing beta zeolite of the present invention may have a BET specific surface area of 490 to 615 m²/g, preferably 500 to 610 m²/g, more preferably 510 to 600 m²/g. In addition, the Ti-containing beta zeolite of the present invention preferably has a pore volume of 0.20 to 0.35 cm³/g, more preferably 0.22 to 0.30 cm³/g. The specific surface area and the volume may be measured using a BET surface area analyzer. The beta zeolite having a specific surface area and a volume in the above ranges can be produced by a preferred method described later.

The Ti-containing beta zeolite of the present invention preferably has a diffraction pattern having diffraction peaks at at least the positions shown in Tables 1 and 2 below, in which the diffraction pattern is obtained by X-ray diffraction using Cu—Kα₁ rays. In this regard, Table 1 shows the diffraction pattern, and Table 2 shows preferred peak intensity ratios. In Table 1, "vs" indicates very strong relative intensity (80 to 100%), "s" strong relative intensity (60 to 80%), "m" moderately strong relative intensity (40 to 60%), "w" weak relative intensity (0 to 40%), and in Table 2, the peak intensity (%) indicates the intensity relative to the intensity of the maximum peak, which is normalized to 100, in the diffraction pattern. As used therein, the term "peak intensity ratio" refers to the ratio between peak heights.

TABLE 1

| Peak Position 2θ (°) | Relative Peak Intensity |
|---|---|
| 21.08 to 21.58 | w |
| 22.12 to 22.62 | vs |
| 25.00 to 25.50 | w |
| 26.80 to 27.30 | w |
| 28.38 to 28.88 | w |
| 29.26 to 29.86 | w |
| 30.00 to 30.70 | w |
| 32.92 to 33.62 | w |
| 43.00 to 43.85 | w |

TABLE 2

| Peak Position 2θ (°) | Relative Peak Intensity (%) |
|---|---|
| 21.08 to 21.58 | 9 to 29, preferably 17 to 15 |
| 22.12 to 22.62 | 100 |
| 25.00 to 25.50 | 6 to 26, preferably 14 to 16 |
| 26.80 to 27.30 | 4 to 24, preferably 14 to 15 |
| 28.38 to 28.88 | 3 to 23, preferably 11 to 13 |
| 29.26 to 29.86 | 2 to 22, preferably 12 to 14 |
| 30.00 to 30.70 | 1 to 16, preferably 5 to 6 |
| 32.92 to 33.62 | 1 to 18, preferably 8 |
| 43.00 to 43.85 | 1 to 20, preferably 10 |

The beta zeolite having relative peak intensities in the above ranges can be produced by a preferred method described below.

The Ti-containing beta zeolite of the present invention is advantageously produced by the method described below. Specifically, a preferred method for producing the Ti-containing beta zeolite of the present invention includes four steps: (1) performing an ion exchange treatment on a raw material beta zeolite; (2) exposing the ion-exchanged raw material beta zeolite to water vapor; (3) performing an acid treatment on the raw material beta zeolite having undergone the exposure to water vapor; and (4) introducing Ti.

(1) Step of Performing Ion Exchange Treatment on Raw Material Beta Zeolite

The raw material beta zeolite usually contains alkali metals such as sodium. The alkali metal-containing beta zeolite is converted into an ammonium-type beta zeolite by ion exchange for removal of the alkali metal, because it cannot well provide the desired performance when used as a catalyst in the petrochemical industry or as a carbon trap for purifying exhaust gas from internal combustion engines.

The raw material beta zeolite to be subjected to the ion exchange treatment preferably has a low Si/Al molar ratio, such as a Si/Al molar ratio of 4 to 8, preferably 4.5 to 6.5, more preferably 4.6 to 6.1. This is because the beta zeolite with a Si/Al molar ratio in such ranges can easily form the Ti-containing beta zeolite with the specific features described above.

When the raw material beta zeolite used is one synthesized without using any organic SDA (hereinafter also referred to as "OSDA-free beta zeolite"), a Ti-containing beta zeolite having high catalytic activity can be obtained. The use of the OSDA-free beta zeolite is also advantageous in terms of economy and environmental impact in that no OSDA is used.

For example, the method disclosed in WO 2011/013560 may be used to synthesize the OSDA-free beta zeolite. The method disclosed in Chinese Patent Application Publication No. 101249968 A may also be used. In addition, the method described in Chemistry of Materials, Vol. 20, No. 14, pp. 4533-4535 (2008) may be used.

An example of a method for synthesizing the OSDA-free beta zeolite includes:
(i) mixing a silica source, an alumina source, an alkali source, and water to form a reactant mixture having a composition represented by the following molar ratios: $SiO_2/Al_2O_3$=40 to 200, particularly, 44 to 200; $Na_2O/SiO_2$=0.22 to 0.4, particularly, 0.24 to 0.35; $H_2O/SiO_2$=10 to 50, particularly, 15 to 25;
(ii) adding 0.1 to 20% by mass of a seed crystal of a beta zeolite to the reactant mixture based on the mass of the silica component in the reactant mixture, in which the beta zeolite has a $SiO_2/Al_2O_3$ ratio of 8 to 30 and a mean particle size of 150 nm or more, specifically 150 to 1,000 nm, in particular 200 to 600 nm and is free of any organic compound; and
(iii) heating the seed crystal-containing reactant mixture at 100 to 200° C., in particular 120 to 180° C. in a hermetic system.

An ammonium compound may be used for the ion exchange of the raw material beta zeolite. In particular, ammonium nitrate, ammonium chloride, ammonium acetate, or ammonium sulfate is preferably used. The ion exchange may be performed under conditions where an ammonium ion-containing aqueous solution is heated or not heated. The raw material beta zeolite may be dispersed in the ammonium ion-containing aqueous solution to form a dispersion, and the ion exchange may be performed by maintaining the dispersed state for a predetermined period of time.

After maintained for a predetermined period of time, the dispersion may be filtered so that the raw material beta zeolite is separated, which may then be washed with water. If necessary, the combination of the ion exchange treatment and the washing with water may be performed a plurality of times. After the ion exchange treatment is performed in this manner, the raw material beta zeolite may be dried to give an ammonium-type beta zeolite. The resulting ammonium-type beta zeolite has a greatly reduced alkali metal ion content.

(2) Step of Exposing Ion-Exchanged Raw Material Beta Zeolite to Water Vapor

The step of exposing the raw material beta zeolite of the ammonium type to water vapor may be performed by, for example, allowing the raw material beta zeolite to stand in a water vapor atmosphere or placing the raw material beta zeolite in a stream of water vapor. Specifically, an apparatus shown in FIG. 1 may be used to expose the raw material beta zeolite to water vapor. The apparatus 10 shown in FIG. 1 includes a holding tube 11 in which the raw material beta zeolite is held. The holding tube 11 is open at both ends. Its lower end 11b is open to the atmosphere. The upper end 11a of the holding tube 11 forms an inlet for water vapor and is connected to a water vapor supply source 12 and an inert gas supply source 13. The water vapor supply source 12 includes a bottomed cylindrical body 12a open at an upper end. One end of an inert gas bubbling tube 12b is inserted in the cylindrical body 12a. The other end of the bubbling tube 12b is connected to an inert gas supply source (not shown). Water 14 is placed in the cylindrical body 12a. The surface level of the water is higher than the position of the end of the bubbling tube 12b inserted in the bottomed cylindrical body 12a. A heater 15 is provided around the holding tube 11. The heater 15 allows heating the raw material beta zeolite in the holding tube 11 and heating water vapor flowing through the holding tube 11. While an inert gas such as argon is supplied from the inert gas supply source 13, an inert gas is bubbled through the bubbling tube 12b into the water in the water vapor supply source 12 so that a predetermined amount of water vapor is supplied into the holding tube 11. The amount of supply of the water vapor is determined by the balance between the amount of supply of the inert gas from the inert gas supply source 13 and the amount of supply of the inert gas into the water vapor supply source 12. The water vapor supplied into the holding tube 11 is heated together with the raw material beta zeolite by the heater 15. Thus, the raw material beta zeolite is exposed to water vapor heated to a predetermined temperature. The exposure probably causes aluminum atoms in the raw material beta zeolite to leave certain sites in the crystal lattice and causes silicon atoms to migrate to the sites that the aluminum atoms have left. At the time of the exposure to water vapor, however, there is little change in the Si/Al ratio of the raw material beta zeolite. In addition, when exposed to water vapor, the raw material beta zeolite is converted from the ammonium type to a proton type.

Figure 1:
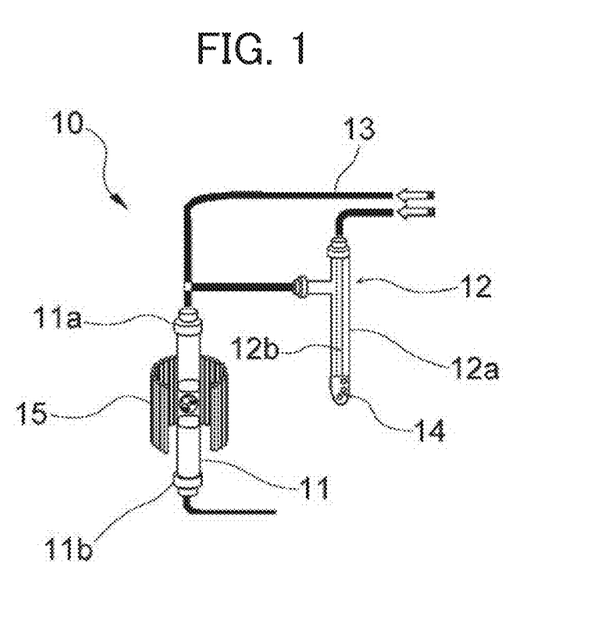
FIG. 1 is a schematic view showing an apparatus for use in exposure of a beta zeolite to water vapor.

The water vapor to which the raw material beta zeolite is exposed preferably has a temperature of 250 to 700° C., more preferably 400 to 600° C., in particular preferably 450 to 550° C. so that the aluminum leaving can be enhanced while the crystal structure of the zeolite is prevented from being destroyed. For the same reason, the exposure to water vapor is preferably performed for a time period of 12 to 48 hours, more preferably 18 to 36 hours, in particular preferably 22 to 26 hours. At the time point when the water vapor comes into contact with the raw material beta zeolite, the water vapor has a pressure (partial pressure) equal to or lower than the atmospheric pressure, because the holding tube 11 is open at the lower end. The partial pressure of the water vapor is preferably 8 to 12 kPa.

(3) Step of Performing Acid Treatment on Raw Material Beta Zeolite Having Undergone Exposure to Water Vapor The raw material beta zeolite having undergone the exposure to water vapor is subjected to an acid treatment, which causes dealumination of the beta zeolite. Various mineral acids may be preferably used in the acid treatment. For example, nitric acid, sulfuric acid, hydrochloric acid, and so on may be used. As the acid concentration in the acid treatment increases, dealumination proceeds more to increase the Si/Al ratio of the beta zeolite. Therefore, controlling the acid concentration is a simple method for obtaining the beta zeolite with a desired Si/Al molar ratio. In this point of view, the acid concentration is often preferably 10 to 98% by mass, in particular preferably 30 to 70% by mass, depending on the type of the acid used. For example, when nitric acid is used as the mineral acid, the nitric acid concentration is preferably 55 to 65% by mass, in particular preferably 59 to 62% by mass. When nitric acid is used as the mineral acid, the molar concentration of nitric acid is preferably 12.0 to 14.2 mol/L, in particular preferably 12.9 to 13.6 mol/L. In order to obtain a Ti-containing beta zeolite having high catalytic activity, the beta zeolite after the acid treatment preferably has a Si/Al molar ratio of 100 or more, more preferably 300 or more, in particular preferably 500 or more.

Regarding the quantity of the acid in the acid treatment, the acid with the above concentration is preferably used in a quantity of 20 to 40 mL, more preferably 25 to 35 mL, in particular preferably 28 to 32 mL per 1 g of the raw material beta zeolite, so that dealumination can occur efficiently. The acid treatment may be performed with or without heating. The acid treatment may be performed with heating using an oil bath. In this case, the temperature of the oil bath is preferably set to 120 to 140° C., in particular preferably 125 to 135° C., for efficient dealumination. When nitric acid is used as the mineral acid, the temperature of the nitric acid is preferably set to 120 to 140° C., in particular preferably 125 to 135° C., depending on its concentration. When the acid treatment is performed with heating, the acid may be refluxed. When the concentration and temperature of the acid are in the above ranges, the acid treatment is preferably performed for a time period of 12 to 36 hours, in particular preferably 20 to 28 hours, for efficient dealumination with prevention of destruction of the zeolite crystal structure. After the acid treatment is completed, solid-liquid separation may be performed. The beta zeolite separated by filtration may be washed with water one or more times and then dried.

Then the step (4) of introducing Ti is performed. A method of introducing Ti includes, for example, bringing the beta zeolite obtained in the step (3) into contact with a gaseous form (gas phase) of titanium chloride or alkoxide. Examples of titanium chloride include $TiCl_4$ and $TiCl_3$, and examples of titanium alkoxide include $Ti(OMe)_4$, $Ti(OEt)_4$, $Ti(OPr)_4$, $Ti(OPr-i)_4$, and $Ti(OBu)_4$. The contact treatment is preferably performed at 500 to 700° C., more preferably at 550 to 650° C. The duration of the contact treatment is preferably 0.5 to 2 hours, more preferably 0.8 to 1.2 hours. The contact treatment is preferably performed in a dry inert gas atmosphere such as Ar, $N_2$, or He. The flow rate of titanium chloride or titanium alkoxide in the gas phase is preferably 0.015 mmol/min to 0.025 mmol/min.

In this way, the desired beta zeolite is obtained. The resulting beta zeolite is an OSDA-free beta zeolite and has a very high Si/Al ratio with the original crystal structure maintained.

The Ti-containing beta zeolite of the present invention is a promising candidate as a solid acid catalyst or an adsorbent, and more specifically, is useful as a catalyst for oxidation of hydrocarbons. In particular, the Ti-containing beta zeolite of the present invention is advantageous in that it not only has a high catalytic activity as a catalyst for epoxidation of olefins or oxidation of unsaturated alicyclic compounds like conventional beta zeolites but also has a catalytic activity for oxidation of, for example, phenols, which most conventional beta zeolites do not have. The reason why the Ti-containing beta zeolite of the present invention has a catalytic activity that is hardly achieved by conventional zeolites is probably that the Ti-containing beta zeolite of the present invention is highly defective as compared to conventional Ti-containing beta zeolites.

Examples of phenols include phenol and phenols having a benzene ring with one or more of the hydrogen atoms substituted by an alkyl group of 1 to 8 carbon atoms, halogen atoms, an alkoxy group, an alkylamino group, or other groups. When the Ti-containing beta zeolite of the present invention is used as a catalyst for oxidation of phenols, an oxidizing agent for use therewith may be, for example, hydrogen peroxide, tert-butyl hydroperoxide, di-tert-butyl peroxide, or dibutyl peroxide, in which hydrogen peroxide is preferred in terms of cost and environmental impact.

When the Ti-containing beta zeolite of the present invention is used as a catalyst for oxidation of phenols, selection of solvents for use in the oxidation reaction of phenols is also preferred for reaction product selectivity. For example, when the catalyst is used for oxidation of phenol as one of the phenols, a cosolvent for use therewith is preferably a polar solvent such as acetonitrile or alcohol, in particular preferably alcohol, so that hydroquinone can be produced with high productivity as compared to catechol. On the other hand, when no polar solvent is used for the oxidation reaction of phenol, hydroquinone can be produced with high productivity as compared to catechol.

In addition, the Ti-containing beta zeolite of the present invention not only has a high catalytic activity for oxidation of phenols as described above but also is suitable for use as a catalyst for epoxidation of olefins. Examples of olefins include those having a carbon-carbon double bond at the end of a hydrocarbon chain and those having a carbon-carbon double bond in a main or side chain or a cyclic hydrocarbon ring. Preferred examples of olefins include those having 2 to 10 carbon atoms, such as ethylene, propylene, 1-butene, 2-butene, isobutylene, 1-pentene, 2-pentene, cyclopentene, 1-hexene, cyclohexene, vinylcyclohexene, allyl alcohol, 1-heptene, 1-octene, 1,3-butadiene, 2-hexene, and cyclooctene.

Like conventional Ti-containing beta zeolites, the Ti-containing beta zeolite of the present invention also has a sufficiently high catalytic activity for oxidation of unsaturated alicyclic compounds such as cyclohexene and cyclooctene.

EXAMPLES

Hereinafter, the present invention will be described in more detail with reference to examples. It will be understood that the examples are not intended to limit the scope of the present invention. Unless otherwise specified, "%" means "% by mass". In the examples shown below, composition analysis was performed using ICPE-9000 manufactured by Shimadzu Corporation.

X-ray diffraction was performed using Ultima IV manufactured by Rigaku Corporation, Cu K$\alpha_1$ rays, and the conditions of voltage 40 kV, current 20 mA, scanning step 0.02°, and scanning speed 2.0°/min.

UV spectra were measured using V-550 manufactured by JASCO Corporation and the conditions of band width 5.0 nm, scanning speed 100 nm/min, and data sampling interval 1 nm.

$^{29}$Si DD MAS NMR spectra were measured using AVANCE III 600 manufactured by Bruker Corporation and the conditions of D=30 s, 2,048 times, hexamethyltricyclosiloxane (at −9.66 ppm) as a reference, 4 mm VTN probe, and MASR=10 kHz.

Nitrogen adsorption-desorption isotherms, BET specific surface areas, and pore volumes were measured using BELSORP-max-1N system manufactured by MicrotracBEL Corp. and the conditions of measurement temperature −196° C. (using 99.999% nitrogen gas), thermostatic air chamber temperature 40° C., and equilibrium adsorption time 300 s, and sample pretreatment conditions including heat treatment at $4.44 \times 10^{-5}$ Pa (400° C., 12 h).

Water vapor adsorption-desorption isotherms were measured using BELSORP-max-12-N-VRYK system manufactured by MicrotracBEL Corp. and the conditions of measurement temperature 25° C. (using water vapor from degassed pure water), thermostatic air chamber temperature 40° C., and equilibrium adsorption time 300 s, and sample pretreatment conditions including heat treatment at $4.44\times10^{-5}$ Pa (400° C., 12 h).

Preparation Example 1

(1) Synthesis of Seed Crystals

According to a conventionally known method, tetraethylammonium hydroxide as an organic SDA, sodium aluminate as an alumina source, and silica fine powder (Mizukasil P707) as a silica source were heated with stirring at 165° C. for 96 hours to form a beta zeolite with a $SiO_2/Al_2O_3$ molar ratio of 24.0. In an electric oven through which air was circulated, the product was fired at 550° C. for 10 hours to form organic-free crystals. As a result of observation with a scanning electron microscope, the crystals had a mean particle size of 280 nm. The resulting organic-free beta zeolite crystals were used as seed crystals.

(2) Synthesis of OSDA-Free Beta Zeolite

In 13.9 g of pure water were dissolved 0.235 g of sodium aluminate and 1.828 g of 36% sodium hydroxide to form an aqueous solution. A mixture of 2.024 g of silica fine powder (Cab-O-sil, M-5) and 0.202 g of the seed crystals was added little by little to the aqueous solution and stirred to form a reactant mixture. The reactant mixture had a $SiO_2/Al_2O_3$ molar ratio of 70, a $Na_2O/SiO_2$ molar ratio of 0.3, and a $H_2O/SiO_2$ molar ratio of 20. The reactant mixture was placed in a 60 mL stainless steel closed vessel and statically heated at 140° C. for 34 hours under autogenous pressure without aging and stirring. After the closed vessel was cooled, the product was collected by filtration and washed with warm water to give a white powder. The product was subjected to X-ray diffraction measurement and as a result, determined to be an impurity-free beta zeolite. Composition analysis showed that the product had a Si/Al molar ratio of 5.8.

Example 1

(1) Ion Exchange Treatment

The OSDA-free beta zeolite obtained in Preparation Example 1 was used as a raw material and dispersed in an aqueous solution of 0.499 mol/L ammonium nitrate. The mass ratio between the OSDA-free beta zeolite, ammonium nitrate, and water was 1:2:50. While heated at 80° C., the dispersion was allowed to stand for 24 hours so that it underwent ion exchange. Filtration was then performed to separate the beta zeolite. The ion exchange-filtration process was performed once again and followed by washing with water and drying at 80° C., so that an ammonium-type beta zeolite was obtained. Composition analysis showed that it had a Si/Al molar ratio of 6.0.

(2) Exposure to Water Vapor

The ammonium-type beta zeolite was charged into the apparatus shown in FIG. 1. The amount of the charged material was 1 g. As shown in FIG. 1, a mixed gas of argon and water vapor was continuously allowed to flow through for 24 hours with heating at 500° C. by the heater 15. The partial pressure of the water vapor was 10 kPa. By the exposure to the water vapor, the beta zeolite was converted from the ammonium type to a proton type. Composition analysis showed that it had a Si/Al molar ratio of 5.9.

(3) Acid Treatment

After the exposure to the water vapor, 0.8 g of the beta zeolite was placed in an eggplant-shaped glass flask, and then 24 mL of an aqueous solution of 13.4 mol/L nitric acid was added to the eggplant-shaped flask. The eggplant-shaped flask was then placed in an oil bath at 130° C. and subjected to reflux with stirring for 24 hours. Subsequently, the mixture was filtered, and the solid on the filter was washed with distilled water until the washings were neutral. The solid was then dried to give an acid-treated beta zeolite. The acid-treated beta zeolite had a Si/Al molar ratio of at least 1,000.

(4) Introduction of Ti

In a heater, 300 mg of the beta zeolite obtained in the step (3) was fixed inside a quartz tube whose temperature was adjustable and heated at 500° C. while Ar gas was allowed to flow therethrough for 4 hours. The temperature was then raised to 600° C. in 30 minutes. Subsequently, at 600° C., Ar gas was allowed to flow through titanium tetrachloride (manufactured by Wako Pure Chemical Industries, Ltd.) to form an Ar gas stream containing $TiCl_4$ vapor, which was allowed to flow through the sample for 1 hour. The $TiCl_4$ flow rate was 0.0204 mmol/min. At the same temperature, Ar gas was allowed to flow through for 1 hour to remove the $TiCl_4$ remaining unreacted in the sample. After allowed to cool to room temperature, the resulting sample was thoroughly washed with distilled water and dried to give a desired Ti-containing beta zeolite.

Figure 2:
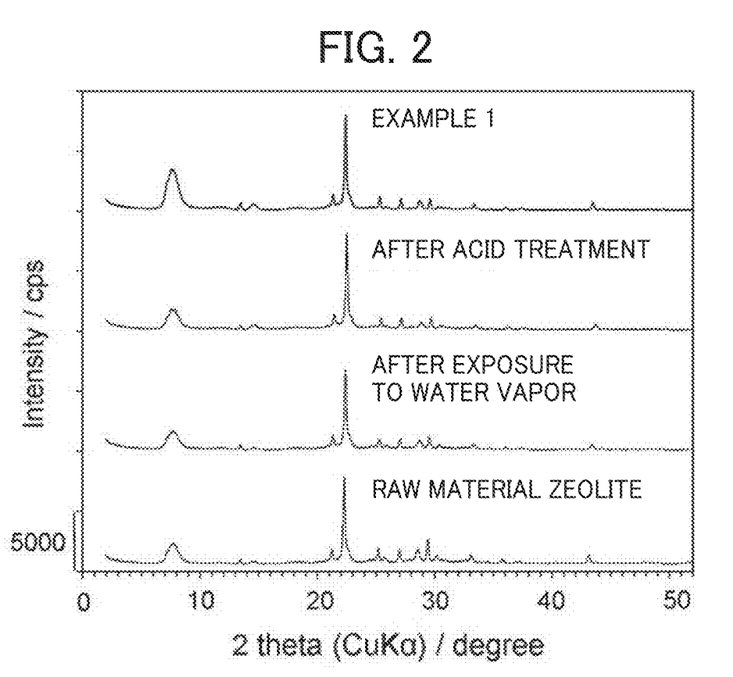
FIG. 2 is a graph showing X-ray diffraction diagrams for a Ti-containing beta zeolite of Example 1.

Composition analysis showed that the resulting Ti-containing beta zeolite had a Si/Al molar ratio of at least 1,000, a Si/Ti molar ratio of 67.8, and a Ti content of 0.24 mmol/g. The resulting Ti-containing beta zeolite has a BET specific surface area of 510 m²/g and a pore volume of 0.247 cm³/g. FIG. 2 shows an X-ray diffraction diagram of the resulting Ti-containing beta zeolite. FIG. 2 indicates that the resulting Ti-containing beta zeolite has high crystallinity. Table 3 shows an X-ray diffraction pattern of the resulting Ti-containing beta zeolite. FIG. 2 also shows X-ray diffraction diagrams of the beta zeolites obtained after the respective steps, namely, the OSDA-free, raw material zeolite ($NH_4$ type), the zeolite obtained after the exposure to water vapor, and the zeolite obtained after the acid treatment.

TABLE 3

| Peak Position 2θ (°) | Relative Peak Intensity (%) |
|---|---|
| 21.08 to 21.58 | 19 |
| 22.12 to 22.62 | 100 |
| 25.00 to 26.50 | 16 |
| 26.80 to 27.30 | 14 |
| 28.38 to 28.88 | 13 |
| 29.26 to 29.86 | 12 |
| 30.00 to 30.70 | 6 |
| 32.92 to 33.62 | 8 |
| 43.00 to 43.85 | 10 |

Figure 3:
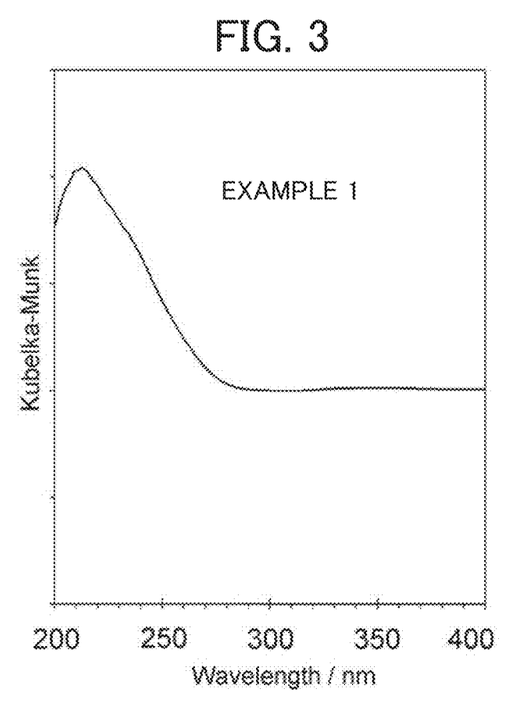
FIG. 3 is a UV spectrum of the Ti-containing beta zeolite of Example 1.

FIG. 3 shows a UV spectrum of the resulting Ti-containing beta zeolite. FIG. 3 shows that the resulting Ti-containing beta zeolite has a peak at about 216 to 217 nm, which indicates tetracoordinated Ti.

Figure 4:
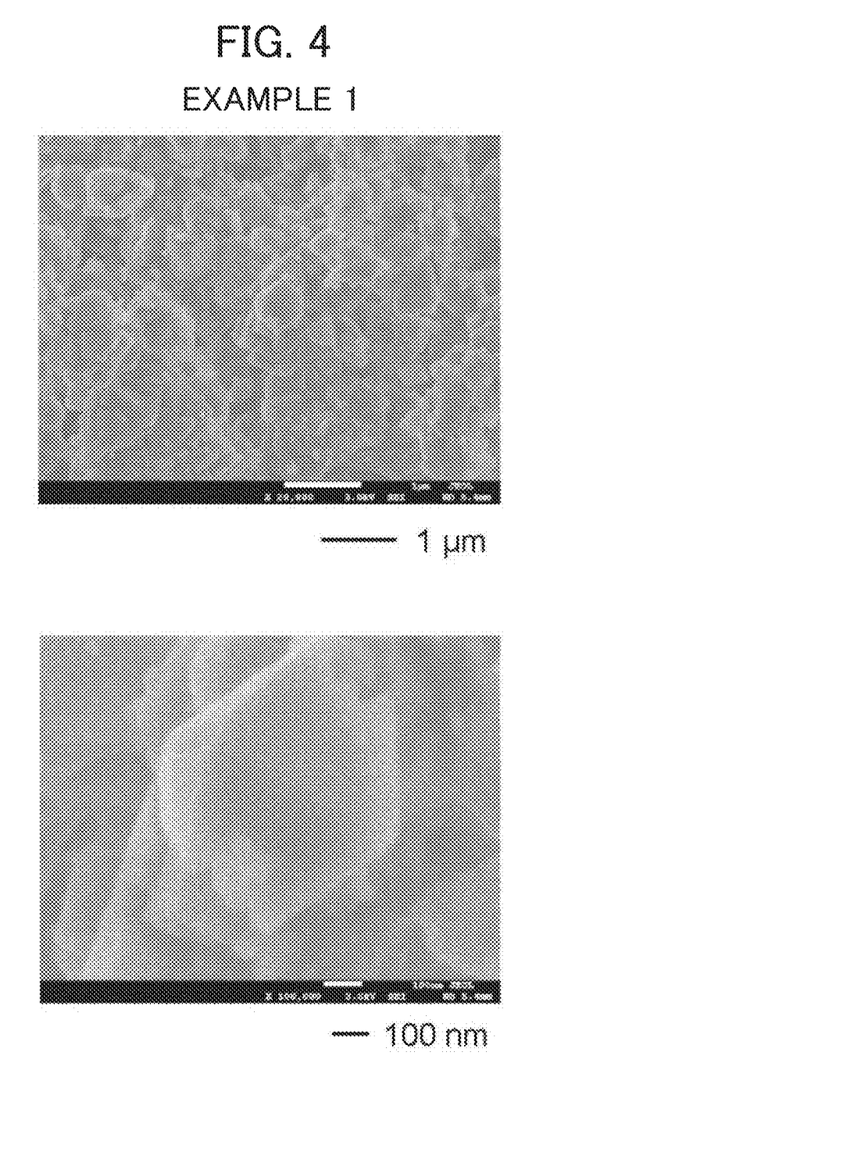
FIG. 4 is an SEM image of the Ti-containing beta zeolite of Example 1.

FIG. 4 shows an SEM image of the resulting Ti-containing beta zeolite. FIG. 4 shows that the resulting beta zeolite particles have an octahedral shape with both opposed edges truncated.

FIG. 5 shows that the resulting Ti-containing beta zeolite has a nitrogen adsorption isotherm at −196° C. that shows a nitrogen absorption of 139 cm³ (STP)/g at a relative pressure $P/P_0$ of 0.4 and shows a nitrogen absorption of 176 cm³ (STP)/g at a relative pressure $P/P_0$ of 0.9, in which P and $P_0$ are respectively the equilibrium pressure and the saturated vapor pressure at a temperature of −196° C.

FIG. 6 shows that the resulting Ti-containing beta zeolite has a water vapor adsorption isotherm at 25° C. that shows a water absorption of 30.4 cm³ (STP)/g at a relative pressure $P/P_0$ of 0.4 and shows a water absorption of 164.4 cm³ (STP)/g at a relative pressure $P/P_0$ of 0.9, in which P and $P_0$ are respectively the equilibrium pressure and the saturated vapor pressure at a temperature of 25° C.

Figure 7:
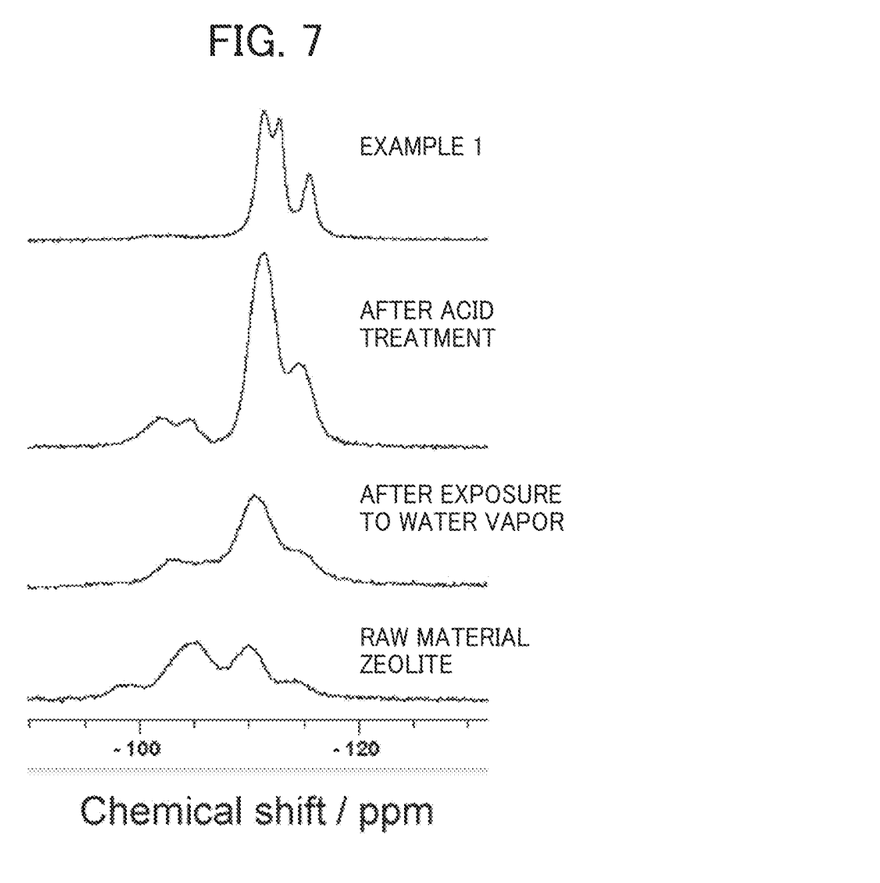
FIG. 7 is a graph showing $^{29}Si$ DD MAS NMR spectra for the Ti-containing beta zeolite of Example 1.

FIG. 7 shows a $^{29}$Si DD MAS NMR spectrum of the resulting Ti-containing beta zeolite. FIG. 7 shows that at least two peaks are observed in the range of −114 ppm to −110 ppm. FIG. 7 also shows that almost no peaks are observed in the range of −108 ppm to −100 ppm.

Example 2

A Ti-containing beta zeolite of Example 2 was obtained similarly to Example 1 except that, in the step (4) of introducing Ti, the beta zeolite obtained in the step (3) was used in an amount of 504 mg instead of 300 mg in Example 1. Composition analysis showed that the Ti-containing beta zeolite of Example 2 had a Ti content of 0.272 mmol/g, a Si/Al molar ratio of at least 1,000, and a Si/Ti molar ratio of 59.9.

Example 3

A Ti-containing beta zeolite of Example 3 was obtained similarly to Example 1 except that, in the step (4) of introducing Ti, the beta zeolite obtained in the step (3) was used in an amount of 506 mg instead of 300 mg in Example 1. Composition analysis showed that the Ti-containing beta zeolite of Example 3 had a Ti content of 0.297 mmol/g, a Si/Al molar ratio of at least 1,000, and a Si/Ti molar ratio of 55.1.

Comparative Example 1

A Ti-containing beta zeolite of Comparative Example 1 was produced according to the method disclosed in Patent Document 3. In the process of preparing the Ti-containing beta zeolite, an aqueous solution of 0.3071 mmol/g of 4,4'-trimethylenebis(1-benzyl-1-methylpiperidinium) dihydroxide was used.

Comparative Example 2

A beta zeolite produced by a dry gel conversion method (crystallization time 24 hours) using TEBOP$^{2+}$ as an organic structure-directing agent was used instead of the beta zeolite obtained in Example 1. A Ti-containing beta zeolite of Comparative Example 2 was obtained similarly to Example 1 except that the above beta zeolite is used as a raw material and that the Ti introduction was performed under the conditions of steaming at 250° C. for 24 hours followed by firing at 450° C. for 3 hours, washing with water, and firing at 500° C. for 1 hour.

Comparative Example 3

Instead of the beta zeolite obtained in Example 1, a Ti-containing beta zeolite of Comparative Example 3 was obtained by performing a fluoride method in the presence of a Ti source using tetraethylammonium as an organic structure-directing agent.

[Evaluation 1]

The Ti-containing beta zeolites obtained in Example 1 and Comparative Examples 1 to 3 were examined for their function as phenol oxidation catalysts by the method described below. In a pressure-resistant glass vessel, 20 mg of the catalyst, 2.0 g (21.25 mmol) of phenol, 0.48 g (4.25 mmol) of hydrogen peroxide water (30 wt %) were mixed and stirred at 100° C. for 10 minutes. After the reaction was completed, the reaction mixture was diluted with 2.0 g (16.6 mmol) of sulfolane while the vessel was cooled with ice. After 0.225 g (2.08 mmol) of anisole as an internal standard was added to the mixture and mixed thoroughly, the reaction solution and the catalyst were separated by centrifugation (3,500 rpm, 10 minutes).

Subsequently, excess amounts of acetic anhydride (about 0.2 g) and potassium carbonate (about 0.3 g) were added to 100 mg of the supernatant, and the whole of the reactant solution was shaken at 35° C. for 10 minutes so that existing phenolic compounds were thoroughly acetylated. Subsequently, the reaction mixture was diluted with chloroform and then analyzed using a gas chromatograph (GC-2014 manufactured by Shimadzu Corporation; Detector: FID; Column: DB-1 0.25 mm×30 m×1.00 µm). The unreacted hydrogen peroxide was also quantified as follows: 0.5 g of the centrifugation supernatant and 0.8 g of potassium iodide were added to 50 mL of an aqueous solution of 2 mol/L hydrochloric acid, and then the mixture was titrated with an aqueous solution of 0.1 mol/L sodium thiosulfate. Table 4 shows the Ti content of each catalyst, the catalytic turnover number (TON) of each catalyst, yield, selectivity for para product (p-Sel. (%)), selectivity for ortho product (o-Sel. (%)), and efficiency for $H_2O_2$ ($H_2O_2$ Conv. Eff. (%)).

TABLE 4

| Zeolite | Ti content (mmol/g) | TON$^a$ | yield (%)$^b$ total | HQ | CL | p-BQ | p-sel. (%)$^c$ | o-sel. (%)$^d$ | $H_2O_2$ (%) conv. | eff.$^e$ |
|---|---|---|---|---|---|---|---|---|---|---|
| Example 1 | 0.240 | 201 | 22.2 | 3.3 | 14 | 4.9 | 36.9 | 63.1 | 44.4 | 48.3 |
| Example 2 | 0.272 | 147 | 18.7 | 2.6 | 12.1 | 4 | 35.4 | 64.6 | 33.6 | 53.7 |
| Example 3 | 0.297 | 173 | 23.6 | 3.5 | 14.8 | 5.3 | 37.3 | 62.7 | 45.9 | 49.7 |
| Comparative Example 1 | 0.329 | 23 | 3.5 | 0.3 | 0.9 | 2.3 | 74.1 | 25.9 | 26.6 | 12.7 |
| Comparative Example 2 | 0.269 | 0 | <0.1 | <0.1 | <0.1 | <0.1 | — | — | 32.7 | <0.1 |

TABLE 4-continued

| Zeolite | Ti content (mmol/g) | TON[a] | yield (%)[b] | | | | p-sel. (%)[c] | o-sel. (%)[d] | $H_2O_2$ (%) | |
| --- | --- | --- | --- | --- | --- | --- | --- | --- | --- | --- |
| | | | total | HQ | CL | p-BQ | | | conv. | eff.[e] |
| Comparative Example 3 | 0.118 | 0 | <0.1 | <0.1 | <0.1 | <0.1 | — | — | 4.4 | <0.1 |

[a]Turnover number, (HQ + CL + p-BQ)-mol/Ti-mol.
[b]After exhaustive acetylation of the products with excess $Ac_2O$—$K_2CO_3$, the derivatized products were analyzed by GC (0.25 mm × 30 m × 1.00 μm DB-1 column, internal standard: anisole, detector: FID).
[c]para selectivity = mol-(HQ + p-BQ)/mol-(HQ + CL + p-BQ).
[d]ortho selectivity = mol-(CL)/mol-(HQ + CL + p-BQ).
[e]$H_2O_2$ efficiency = (HQ + CL + p-BQ)-mol/($H_2O_2$ converted)-mol.

Table 4 shows that the yield of phenol oxides obtained using the Ti-containing beta zeolites of Comparative Examples 1 to 3, which were obtained using an organic structure-directing agent, was as low as at most 3.5%, whereas the yield of phenol oxides obtained using the Ti-containing beta zeolites of Examples 1 to 3, which were synthesized without using any organic structure-directing agent, was at least 18.7%. This indicates that the Ti-containing beta zeolite of the present invention has high catalytic performance for oxidation of phenol.

[Evaluation 2]

The Ti-containing beta zeolite of Example 1 was subjected to Evaluation Examples 2-1 to 2-4 described below.

Evaluation Example 2-1

Phenol oxidation reaction was performed using a method similar to that in Evaluation 1, except that stirring at 70° C. for 60 minutes was performed instead of the stirring in Evaluation 1.

Evaluation Examples 2-2 to 2-4

Phenol oxidation reaction was performed using a method similar to that in Evaluation Example 2-1, except that 4.0 g of the cosolvent shown in Table 2 was added into the pressure-resistant glass vessel containing the catalyst, phenol, and hydrogen peroxide water and that the reaction temperature and the reaction time were changed to 70° C. and 60 minutes.

Table 5 shows catalytic turnover number (TON), yield, selectivity for para product (p-Sel. (%)), selectivity for ortho product (o-Sel. (%)), and efficiency for $H_2O_2$ ($H_2O_2$ Conv. Eff. (%)), which were determined from the measurement results obtained in Evaluation Examples 2-1 to 2-4.

Table 5 indicates that, when used in combination with a cosolvent, in particular alcohol, the Ti-containing beta zeolite of the present invention can provide enhanced para-selectivity in the phenol oxidation reaction.

Example 4

Figure 8:
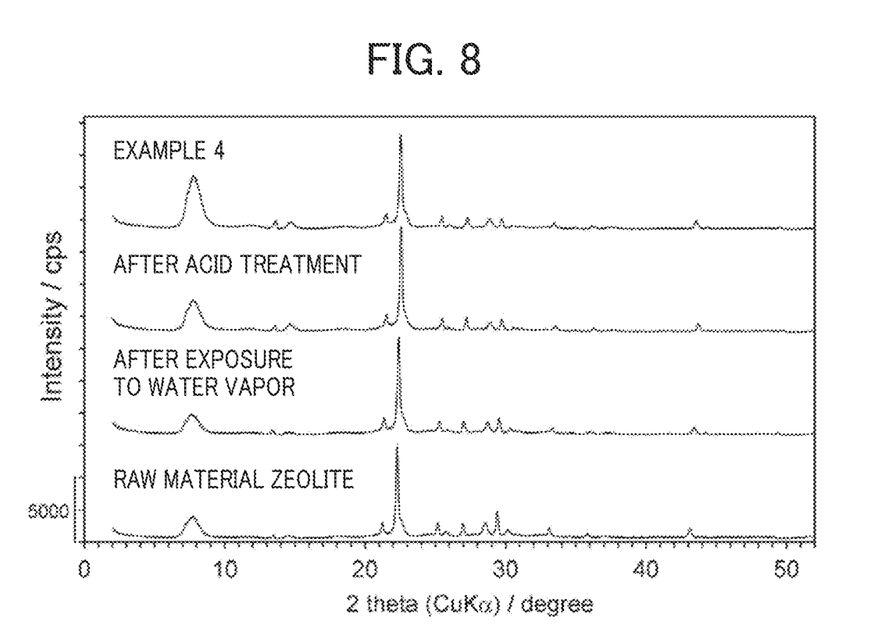
FIG. 8 is a graph showing X-ray diffraction diagrams for a Ti-containing beta zeolite of Example 4.

A Ti-containing beta zeolite was obtained similarly to Example 1 except that, in the step (4) of introducing Ti, the beta zeolite obtained in the step (3) was used in an amount of 296 mg instead of the amount in Example 1. Composition analysis showed that the Ti-containing beta zeolite had a Ti content of 0.211 mmol/g, a Si/Al molar ratio of at least 1,000, and a Si/Ti molar ratio of 85.2. FIG. 8 shows an X-ray diffraction diagram of the Ti-containing beta zeolite of Example 4. Table 6 shows an X-ray diffraction pattern of the Ti-containing beta zeolite, which is based on FIG. 8.

TABLE 6

| Peak Position 2θ (°) | Relative Peak Intensity |
| --- | --- |
| 21.08 to 21.58 | w |
| 22.12 to 22.62 | vs |
| 25.00 to 25.50 | w |
| 26.80 to 27.30 | w |
| 28.38 to 28.88 | w |
| 29.26 to 29.86 | w |
| 30.00 to 30.70 | w |
| 32.92 to 33.62 | w |
| 43.00 to 43.85 | w |

Comparative Example 4

A Ti-containing beta zeolite of Comparative Example 4 was obtained similarly to Comparative Example 1 except as

TABLE 5

| Zeolite | Evaluation Example No. | Cosolvent | TON[a] | yield (%)[b] | | | | p-sel. (%)[c] | $H_2O_2$ (%) | |
| --- | --- | --- | --- | --- | --- | --- | --- | --- | --- | --- |
| | | | | Total | HQ | CL | p-BQ | | Conv. | Eff.[d] |
| Example 1 | 2-1 | none | 68 | 8.1 | 1.4 | 5 | 1.7 | 38.1 | 22.9 | 34.4 |
| | 2-2 | EtOH | 46 | 5.2 | 1.5 | 1.3 | 2.4 | 75.5 | 6.9 | 73.6 |
| | 2-3 | i-PrOH | 17 | 2.2 | 0.7 | 0.8 | 0.7 | 61.3 | 7.9 | 26.8 |
| | 2-4 | $CH_3CN$ | 51 | 6.4 | 1.2 | 3.2 | 1.9 | 49.8 | 5.3 | >99 |

[a]Turnover number, (HQ + CL + p-BQ)-mol/Ti-mol.
[b]After exhaustive acetylation of the products with excess $Ac_2O$—$K_2CO_3$, the derivatized products were analyzed by GC (0.25 mm × 30 m × 1.00 μm DB-1 column, internal standard: anisole, detector: FID).
[c]para selectivity = mol-(HQ + p-BQ)/mol-(HQ + CL + p-BQ).
[d]$H_2O_2$ efficiency = (HQ + CL + p-BQ)-mol/($H_2O_2$ converted)-mol.

follows. In the process of preparing the Ti-containing beta zeolite, an aqueous solution of 0.4115 mmol/g of 4,4'-trimethylenebis(1-benzyl-1-methylpiperidinium) dihydroxide was used.

[Evaluation 3]

The Ti-containing beta zeolites of Example 4 and Comparative Example 4 were subjected to a phenol oxidation reaction test similar to that in Evaluation 1. Table 7 shows the results.

TABLE 7

| Zeolite | Ti content (mmol/g) | TON[a] | Yield (%)[b] total | HQ | CL | p-BQ[c] | $H_2O_2$ (%) Conv. | Eff.[d] |
|---|---|---|---|---|---|---|---|---|
| Comparative Example 4 | 0.428 | 6 | 1 | 0.2 | 0.2 | 0.6 | 34.4 | 3 |
| Example 4 | 0.211 | 118 | 11.8 | 0.2 | 10.5 | 1.1 | 60.2 | 19 |

[a]Turnover number, (HQ + CL + p-BQ)-mol/Ti-mol.
[b]After exhaustive acetylation of the products with excess $Ac_2O$—$K_2CO_3$, the derivatized products were analyzed by GC (0.25 mm × 30 m × 1.00 µm DB-1 column, internal standard: anisole, detector: FID).
[c]para selectivity = mol-(HQ + p-BQ)/mol-(HQ + CL + p-BQ).
[d]$H_2O_2$ efficiency = (HQ + CL + p-BQ)-mol/($H_2O_2$ converted)-mol.

The results in Table 7 indicate that, even when produced under different conditions, the beta zeolite of the present invention can provide a catalytic activity significantly higher than that of conventional beta zeolites.

[Evaluation 4]

The Ti-containing beta zeolites obtained in Example 4 and Comparative Examples 3 and 4 were examined for their function as olefin epoxidation catalysts by the method described below. In a pressure-resistant glass vessel, 25 mg of the catalyst, 5.00 mmol of 1-hexene, 0.5486 g (5.0 mmol) of hydrogen peroxide water (30 wt %), 5 mL of acetonitrile, and 0.4 mL of water were mixed and stirred at 60° C. for 2 hours. After the reaction was completed, the vessel was cooled with ice. After 0.225 g of cycloheptanone as an internal standard was added to the mixture and mixed thoroughly, the reaction solution and the catalyst were separated by centrifugation (3,500 rpm, 20 minutes).

The supernatant was then sampled as obtained and analyzed using a gas chromatograph (GC-2014 manufactured by Shimadzu Corporation; Detector: FID; Column: DB-5MS 0.25 mm×30 m×0.25 µm). The unreacted hydrogen peroxide was also quantified as follows: 0.5 g of the centrifugation supernatant and 0.8 g of potassium iodide were added to 50 mL of an aqueous solution of 2 mol/L hydrochloric acid, and then the mixture was titrated with an aqueous solution of 0.1 mol/L sodium thiosulfate. Table 8 shows the Ti content of each catalyst, the catalytic turnover number (TON) of each catalyst, yield, selectivity ((%) for each of epoxide and diol), and efficiency for $H_2O_2$ ($H_2O_2$ Conv. Eff. (%)).

TABLE 8

| Zeolite | Ti content (mmol/g) | TON[a] | total | Selectivity (%)[b] epoxide | diol | $H_2O_2$ (%) Conv. | Eff.[c] |
|---|---|---|---|---|---|---|---|
| Comparative Example 4 | 0.428 | 64 | 13.4 | >99 | <0.1 | 31.8 | 42.1 |
| Comparative Example 3 | 0.118 | 31 | 1.9 | >99 | <0.1 | 4.4 | 42.4 |
| Example 4 | 0.211 | 200 | 20 | 98.1 | 1.9 | 26.3 | 76 |

[a](epoxide + diol)-mol/Ti-mol.
[b]products were analyzed by GC (0.25 mm × 30 m × 0.25 µm DB-5MS column, internal standard: cycloheptanone, detector: FID).
[c]$H_2O_2$ efficiency = (epoxide + diol)-mol/($H_2O_2$ converted)-mol.

Table 8 indicates that the zeolite of the present invention can provide a high total yield and at least a certain level of epoxide selectivity and thus serve as a good catalyst for epoxidation of olefins.

[Evaluation 5]

The Ti-containing beta zeolites obtained in Example 4 and Comparative Examples 3 and 4 were examined for their function as cyclohexene oxidation catalysts by the method described below. In a pressure-resistant glass vessel, 25 mg of the catalyst, 5.0 mmol of cyclohexene, 0.5486 g (5.0 mmol) of hydrogen peroxide water (30 wt %), 5 mL of acetonitrile, and 0.4 mL of water were mixed and stirred at 60° C. for 2 hours. After the reaction was completed, the vessel was cooled with ice. After 0.225 g of 3-methylcyclohexanone as an internal standard was added to the mixture and mixed thoroughly, the reaction solution and the catalyst were separated by centrifugation (3,500 rpm, 20 minutes).

The supernatant was then sampled as obtained and analyzed using a gas chromatograph (GC-2014 manufactured by Shimadzu Corporation; Detector: FID; Column: DB-5MS 0.25 mm×30 m×0.25 µm). The unreacted hydrogen peroxide was also quantified as follows: 0.5 g of the centrifugation supernatant and 0.8 g of potassium iodide were added to 50 mL of an aqueous solution of 2 mol/L hydrochloric acid, and then the mixture was titrated with an aqueous solution of 0.1 mol/L sodium thiosulfate. Table 9 shows the Ti content of each catalyst, the catalytic turnover number (TON) of each catalyst, yield, selectivity (%), and efficiency for $H_2O_2$ ($H_2O_2$ Conv. Eff. (%)). In Table 9, the numbers 2 to 6 represent the compounds shown below.

TABLE 9

| Zeolite | TON[a] | Yield (%)[b] | Selectivity(%) 2 | 3 | 4 | 5 | 6 | Triols | $H_2O_2$ (%) Conv. | Eff.[c] |
|---|---|---|---|---|---|---|---|---|---|---|
| Comparative Example 4 | 213 | 45.8 | 53 | 11.2 | 0.9 | 0.5 | 23.9 | 10.5 | 41.5 | >99 |
| Example 4 | 265 | 28.4 | 59.4 | 13.5 | 1.6 | 0.4 | 17.7 | 7.3 | 24.9 | >99 |
| Comparative Example 3 | 86 | 4.9 | 50.7 | 0 | 0 | 0 | 49.3 | 0 | 3.6 | >99 |

[a]Turnover number (moles pf products per mole of Ti-site).
[b]Total product yields determined by GC (column: 0.25 mm × 30 m × 0.25 µm DB-5MS, internal standard: 3-methylcyclohexanone, detector: FID).
[c]Efficiency of $H_2O_2$ utilization (moles of products per mole of $H_2O_2$ converted).

[Chem. 1]

The results in Table 9 indicate that the Ti-containing beta zeolite of the present invention is also useful as a catalyst for oxidation of unsaturated alicyclic compounds.

EXPLANATION OF REFERENCE NUMERALS

10 Apparatus for exposure to water vapor
11 Holding tube
12 Water vapor supply source
13 Inert gas supply source
14 Water
15 Heater

The invention claimed is:

1. A beta zeolite comprising a titanium-containing structural skeleton and having a Ti content of 0.10 mmol/g or more, the beta zeolite being synthesized without using any organic structure-directing agent,
    wherein the beta zeolite has a nitrogen adsorption isotherm at −196° C. that shows a nitrogen absorption of 100 to 175 cm$^3$ (STP)/g at a relative pressure P/P$_0$ of 0.4 and shows a nitrogen absorption of 160 to 220 cm$^3$ (STP)/g at a relative pressure P/P$_0$ of 0.9, in which P and P$_0$ are respectively the equilibrium pressure and the saturated vapor pressure at a temperature of −196° C.

2. The beta zeolite according to claim 1, which has a Si/Ti molar ratio of 20 or more and 200 or less.

3. The beta zeolite according to claim 1, which has a Si/Al molar ratio of 100 or more.

4. An oxidation catalyst comprising the beta zeolite according to claim 1 and being for use in oxidation of phenols.

5. An olefin epoxidation catalyst comprising the beta zeolite according to claim 1.

6. A method for producing the beta zeolite according to claim 1, comprising:
    performing ion exchange on a raw material beta zeolite synthesized without using any organic structure-directing agent to form an ammonium-type beta zeolite;
    then exposing the ammonium-type beta zeolite to water vapor; performing an acid treatment on the beta zeolite after the exposure; and then introducing Ti into the beta zeolite after the acid treatment.

7. The method for producing the beta zeolite according to claim 6, wherein the Ti is introduced by treating the beta zeolite with a gaseous form of titanium chloride after the acid treatment.

8. The method for producing the beta zeolite according to claim 6, wherein the acid treatment is performed to increase a Si/Al molar ratio of the beta zeolite to 300 or more after the exposure to water vapor.

9. A method for oxidation of phenol, comprising oxidizing the phenol using the oxidation catalyst according to claim 4 with an alcohol.

* * * * *